United States Patent
Khuller et al.

(10) Patent No.: US 8,409,619 B2
(45) Date of Patent: Apr. 2, 2013

(54) ORAL DRUG DELIVERY SYSTEM FOR AZOLE, MOXIFLOXACIN AND RIFAMPICIN

(75) Inventors: Gopal Krishan Khuller, Chandigarh (IN); Jitendra Nath Verma, Haryana (IN)

(73) Assignee: Lifecare Innovations Pvt. Ltd., Kolkata (IN)

( * ) Notice: Subject to any disclaimer, the term of this patent is extended or adjusted under 35 U.S.C. 154(b) by 201 days.

(21) Appl. No.: 12/682,698

(22) PCT Filed: Oct. 15, 2008

(86) PCT No.: PCT/IN2008/000675
§ 371 (c)(1),
(2), (4) Date: Aug. 23, 2010

(87) PCT Pub. No.: WO2010/044089
PCT Pub. Date: Apr. 22, 2010

(65) Prior Publication Data
US 2010/0310662 A1    Dec. 9, 2010

(51) Int. Cl.
*A61K 9/14* (2006.01)
*A61K 31/497* (2006.01)

(52) U.S. Cl. .................................. 424/489; 514/254.11

(58) Field of Classification Search ........................ None
See application file for complete search history.

(56) References Cited

FOREIGN PATENT DOCUMENTS

| CN | 1437933 A | 8/2003 |
|---|---|---|
| IN | 765DEL2003 | 2/2003 |
| WO | 0028969 A2 | 5/2000 |

OTHER PUBLICATIONS

Nuermberger, E.L., et al., "Moxifloxacin-containing regimens of reduced duration produce a stable cure in murine tuberculosis", 2004, Am. J. Respir Ctir Care Med., 170, pp. 1131-1134.*
Claire du Toit, L., et al., "Tuberculosis chemotherapy: current drug delivery approaches", 2006, Respiratory Research, 7, pp. 1-18.*
Ain, Q., "Role of poly(DL-lactide-co-glycolide] in development of a sustained oral delivery system for antitubercular drug(s)", 2002, Int. J. Pharmaceutics, 239, pp. 37-46.*
Pandey, R., et al., "Nano-encapsulation of azole antifungals potential applications to improve oral drug delivery", 2005, Int. J. Pharmaceutics, 301, pp. 268-276.*
Ahmad et al., "Novel chemotherapy for tuberculosis: chemotherapeutic potential of econazole- and moxifloxacin-loaded PLG nanoparticles", International Journal of Antimicrobial Agents, (Feb. 2008), vol. 31, Issues 2, pp. 142-146.
Janin, "Antituberculosis drugs: Ten years of research", Bioorg. Med. Chem. (2007), pp. 1-35.
Pandey et al., "Oral nanoparticle-based antituberculosis drug delivery to the brain in an experimental model", Journal of Antimicrobial Chemotherapy, (2006), vol. 57, pp. 1146-1152.

\* cited by examiner

*Primary Examiner* — Michael G Hartley
*Assistant Examiner* — Lance Rider
(74) *Attorney, Agent, or Firm* — The Webb Law Firm

(57) ABSTRACT

An oral drug delivery system for treatment of tuberculosis is described. The oral drug delivery system includes (e.g., a mixture or combination of): poly DL-lactide-co-glycolide nano particles having encapsulated an azole therein; poly DL-lactide-co-glycolide nano particles having moxifloxacin encapsulated therein; and poly DL-lactide-co-glycolide nano particles having RIF encapsulated therein.

3 Claims, 1 Drawing Sheet

Plasma drug profile following a single oral
administration of free/PLG nanoparticle encapsulated
moxifloacin or econazole to mice at therapeutic dose
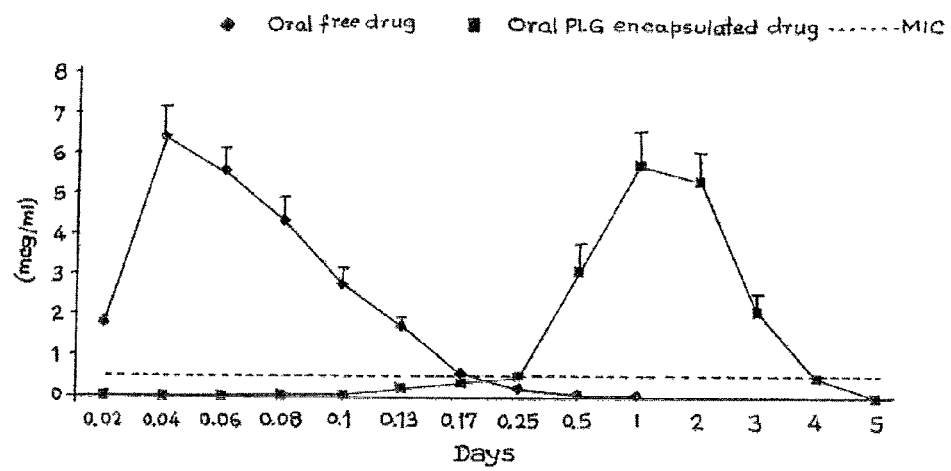
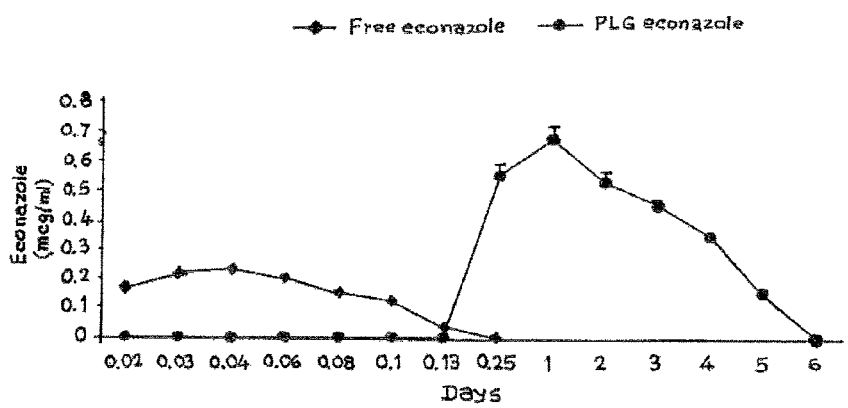
Values are mean S.D of six animals

ORAL DRUG DELIVERY SYSTEM FOR AZOLE, MOXIFLOXACIN AND RIFAMPICIN

TABLE 1

Tissue drug levels on day 6th in mice following a single oral administration of a azole/moifloacin-loaded nanoparticles

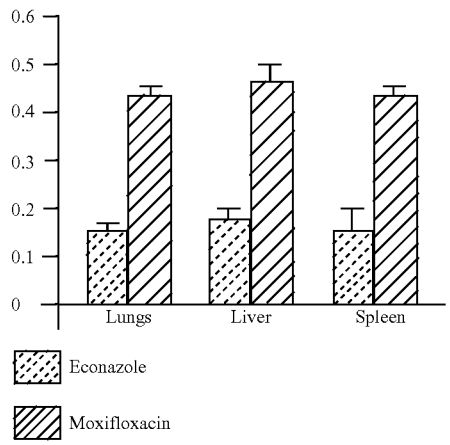

Values are mean S.D of six animals

FIELD OF INVENTION

This invention relates to an oral drug delivery system of poly DL-lactide-co-glycolide nanoparticles (PLG-NP) having active drug separately encapsulated for treatment of tuberculosis. In particular, this invention relates to PLG-NP having azoles and moxifloxacin and RIF separately encapsulated therein.

BACKGROUND OF INVENTION

It is known that azoles possess antifungal properties and was hitherto used only in the form of a cream or ointment for skin infections. Azole has a poor oral bioavailability, and hence could not be effectively employed for the treatment of any Systemic infections.

The use of moxifloxacin as an antituberculosis drug is known in the art. However, moxifloxacin is cleared from the host within 24 hours and, therefore, such a drug is required multiple drug administration on a daily basis resulting in patient non-compliance.

OBJECTS OF THE INVENTION

An object of this invention is to propose an oral drug delivery system of PLG-NP having an azole and moxifloxacin separately encapsulated therein.

Another object of this invention is to propose an oral drug delivery system of PLG-NP having an azole and moxifloxacin separately encapsulated therein which has an enhanced drug bio availability.

Still another object of this invention is to propose an oral drug delivery system of PLG-NP having an azole and moxifloxacin separately encapsulated therein which remains in blood circulation of the host for a longer period.

A further object of this invention is to propose an oral drug delivery system of PLG-NP having an azole and moxifloxacin separately encapsulated therein which is effective against tuberculosis (TB).

A still further object of this invention is to propose an oral drug delivery system of PLG-NP having an azole and moxifloxacin separately encapsulated therein which does not exhibit hepatotoxicity.

SUMMARY OF THE INVENTION

According to this invention there is provided an oral drug delivery system for treatment of tuberculosis comprising (e.g., a mixture or combination of):
  a) poly DL-lactide-co-glycolide nanoparticles having encapsulated at least one azole (e.g., econazole) therein;
  b) poly DL-lactide-co-glycolide nanoparticles having moxifloxacin encapsulated therein; and
  c) poly DL-lactide-co-glycolide nanoparticles having rifampicin (RIF) encapsulated therein.

BRIEF DESCRIPTION OF THE DRAWINGS

FIG. 1 is a graphical representation of plasma drug levels as a function of time.

It is generally known that isoniazid (INH), pyrazinemide (PZA) and rifampicin (RIF) are active substances or drugs employed for the treatment of tuberculosis. Thus, patent application Ser. No. 765/DEL/2003 suggests a process for the simultaneous or co-encapsulation of two or more of the aforesaid drugs, but which are stable with respect to each other.

Besides, the aforesaid three drugs or active substances, it is also known that ethambutol (EMB) is a drug, which is also employed for the treatment of tuberculosis. However, EMB is unstable in the presence of the INH, PZA or RIF, and particularly in the presence of INH. Thus, it has been found that EMB could not be co-encapsulated simultaneously with INH, as any such co-encapsulation would result in a degradation of EMB. Thus, patent application Ser. No. 765/DEL/95 had a useful application for co-encapsulation of active substances or drugs which were compatible to each other with respect to stability.

It has now been found that the normal anti-tubular drugs of INH, PZA and EMB can be replaced by nanoparticles containing separately azole, moxifloxacin and RIF. Thus, the oral drug delivery system consists of separate nanoparticles having moxifloxacin, azole and RIF encapsulated therein. The bioavailability and the retention period in the bloodstream is considerably increased.

Drug loaded PLG nanoparticles were prepared by the multiple emulsion and solvent evaporation technique. Briefly, the active drug was dissolved in distilled water which was then added to dichloromethane (DCM) containing PLG. The mixture sonicated to form the primary emulsion which was poured into aqueous PVA and resonicated. The secondary emulsion so formed was stirred for the removal of DCM, centrifuged to harvest the nanoparticles which were washed with distilled water and vacuum dried.

Secondly, it has now been found that the active drugs when separately encapsulated in nanoparticles, is not eliminated from the body within a few hours, but has a slow release for days together.

In accordance with this invention, the active drug is administered orally in an encapsulated form, but not in the same nanoparticles as the other antitubular drugs.

EXAMPLES

Characterization of ATD-Loaded PLG-Nanoparticles

The particles were characterized for their size and polydispersity index on a Zetasizer 1000 HS (Malvern Instruments, Malvern, UK). The formulation were lysed in 5% w/v SDS in 0.1N NaOH to release the drugs. The percentage drugs encapsulation efficiency was determined by the formula: (amount of drug (mg) released form the nanoparticles/amount of drug (mg) initially taken to prepare the nanoparticles)×100. The drugs were analysed by an HPLC system comprising of a dual-piston reciprocating pump, an online de-gasser, a UV-visual dual wavelength detector (each of Series 200) and a 600 series Link interface for data acquisition/processing, all from Perkin Elimer Instruments LLC (Shelton Conn., USAS). Moxifloxacin was analyzed by employing a USP gradient program (USP 2000) with Water (pH=2.0, set with orthophosphoric acid)' acetonitrile (60/40) as the mobile phase @1.5 (m1/min), 292 nm as the detection wave length and reversed phase C18 column (Cosmosil 5C18-MS-II from Waters; 250×4.6 mm; 5 μm particle size). Econazole and ATDs were analyzed by employing USP gradient/isocratic programs as described earlier. The sensitivity of the methods was: moxifloxacin 0.1 mg/L, econazole 0.2 mg/L, rifampicin 0.4 mg/L.

Preparation of Drugs Doses For In Vivo Studies

The drug doses used throughout the example were moxifloxacin 8 mg/kg, econazole 3.3 mg/kg, rifampicin 12 mg/kg body weight according to the standard adult human doses. The dose being different for each drug, the initial amount of drug taken to prepare the formulations was calculated by the formula: (amount of drug required per animal/mean drug encapsulation efficiency)×100, as previously described. Once the total amount of drugs required was known, an equivalent amount of. PLG was used in the preparation process. PLG nanoparticle formulation encapsulating drugs was suspended in distilled water just before oral dosing in each experiment. Similarly, free drugs were also freshly dissolved in distilled water/methanol (5:1 v/v) immediately before closing.

In Vivo Drug Disposition Studies

Mice were grouped as follows with 12 mice per group: Group 1, free moxifloxacin; Group 2, free econazole; Group 3, free ATDs; Group 4 moxifloxacin loaded PLG nanoparticles; Group 5, econazole loaded PLG nanoparticles; Group 6, ATDs loaded PLG nanoparticles and Group 7, empty PLG nanoparticles (a positive control to explore the influence of PLG nanoparticles on drug estimations). The animals were bled at several time points. The plasma obtained from each mouse was deproteinized and analyzed by HPLC for drugs to obtain the plasma drug concentration versus time profile. The HPLC method for moxifloxacin was same as described above fro encapsulation studies and of other drugs as reported.

The animals were sacrificed at different time points. Drug levels were determined in 20% w/v of tissue homogenates (lungs, liver and spleen) by following the same analytical procedure as described for plasma.

Experimental Infection And Chemotherapy

Mice were infected via the lateral tail vein with $1 \times 10^7$ bacilli of $M.$ $tuberculosis$ $H_{37}R_v$. Fifteen days later, the establishment of infection was confirmed by sacrificing 5 mice and Ziehl-Neelsen staining of lung/spleen homogenates. In addition, 100μ1 of undiluted, 1 in 100 and 1 in 1000 diluted homogenates were placed on Middle brook 7H10 Agar supplemented with OADC for the enumeration of basal colony forming units (cfu). Subsequently, mice were grouped as follows (n=6 per group)—Group 1, untreated control; Group 2, Free econazole twice daily; Group 3, Free moxifloxacin once daily, Group 4, Free econazole+moxifloxacin; and Group 5, free econazole+moxifloxacin+RIF; Group 7, PLG–econazole weekly; Group 8, PLG–econazole+moxifloxacin; Group 9,. PLG–econazole+moxifloxacin+RIF.

On day 62 following the initiation of chemotherapy all the animals were sacrificed. The lungs and spleen were removed aseptically and homogenized in 3 ml sterile isotonic saline. 100μ1 of undiluted, 1 in 100 and 1 in 1000 diluted homogenates were plated on Middle brook media and cfu were counted after 28 days of plating. The cfu data was analyzed by one way analysis of variance (ANOVA) followed by unpaired 't-test' to compare the untreated and treated groups.

Results

Physicohemical Characterization of PLG-Nanoparticles

The average size of PLG nanoparticles was 217 to 250 nm with a polydispersity index of 0.38 to 0.4. The drug encapsulation efficiency of PLG-nanoparticles for econazole and moxifloxacin was found to be 52.27±3.80% and 33.69±3.88% respectively.

In Vivo Drug Disposition

Oral free econazole and moxifloxacin were detectable up to 3-4 and 12 h in plasma respectively. However, following a single oral administration of drug loaded PLG nanoparticles, therapeutic drug concentrations in the plasma were maintained for up to 5 and 4 days in case of econazole and moxifloxacin respectively (FIG. 1), which in the organs (lungs, liver and spleen) both the drugs were detected in therapeutic concentrations for up to 6 days (Table 1). In comparison, free econazole and moxifloxacin were detected in organs up to 12 and 24 h respectively.

Chemotherapy Efficacy

Based on tissue drug distribution free econazole and moxifloxacin were administered twice and once daily while the encapsulated drugs were administered weekly. Al the free ATDs (INH, RIF, PZA and EMB) were administered once daily and encapsulated were administered every $10^{th}$ day with the exception of ethambutol which was administered weekly. Eight weeks of chemotherapy with econazole or moxifloxacin either in free form (112/56 doses, administered twice or once/day) or in encapsulated form (8 doses, administered weekly) resulted in approximately 2 $Log_{10}$ cfu reduction from lungs and spleen of mice as compared to untreated controls (Table 2). Further, the combination of econazole and moxifloxacin proved significantly better than individual drugs as it resulted in the reduction of 3.5 $Log_{10}$ cfu in free or encapsulated form (Table 2). Supplementation of rifampicin to this combination resulted in the most potent regimen that yielded total bacterial clearance in mice with in eight weeks equivalent/comparable to 4ATD's conventional treatment (Table 2).

PLG-nanoparticles encapsulating econazole and moxifloxacin have exhibited immense potential against tuberculosis especially in multidrug resistant and latent or persistent forms of the disease.

A single oral administration of drug (Mox, Eco) loaded PLG-nanoparticles to mice maintained therapeutic drug levels in organs for up to 6 day, this formed the basis of the chemotherapeutic schedule as tuberculosis infection is localized in different tissues. Therefore, PLG-formulation was administered weekly in comparison to free drugs were administered once or twice daily.

Mice were infected with $1.5 \times 10^7$ bacilli of $M.$ $tuberculosis$ $H_{37}R_v$, because similar inoculum has been used in other reports and is known to provide bacillary loads similar to those in human TB cases. Eight weeks of chemotherapy with econazole or moxifloxacin reduced bacterial burden in organs by about 2 log cfu's. Further, PLG-nanoparticles showed their potential to reduce dosing frequency of azoles and moxifloxacin by 14 and 7 fold respectively without compromising therapeutic efficacy. The combination of econazole and moxifloxacin proved to be much better as it reduced bacterial burden by about 3.5 log cfu's compared to 2 log cfu by individual drugs. These results can be explained on the basis that the two drugs have different targets, therefore in combination might act synergistically. Recent studies have shown that econazole inhibits the biosynthesis of glycopeptidolipids (GPLs) which in turn are responsible for maintaining integrity of mycobaterial cell envelope. Thus, econazole might improve the penetration of other drugs like moxifloxacin and make improve the penetration of other drugs like moxifloxacin and make their target (DNA-gyrase in case of moxifloxacin) more accessible. The most interesting finding was the observation that combination of econazole, moxifloxacin and rifampicin resulted in the total bacterial clearance as compared to approximately 7 log cfu in untreated controls. This observation can be explained on the basis of the fact that all three drugs of this combination are active against actively multiplying as well as non dividing bacilli. This combination is more beneficial than conventional regimen on the basis that econazole and moxifloxacin are highly active drug and multidrug resistant bacilli. In addition, all of its three drugs are exhibiting sterilizing actively owing to their activity against non-replicating bacilli as against conventional regimen where only refampicin bears this activity. This regimen is also expected reduce the total duration of tuberculosis chemotherapy owing to sterilizing activity of all its drugs compared to conventional regimen. PLG-nanoparticles have made this new regimen more acceptable as dosing frequency was reduced by 14, 10 and 7 fold for econazole, moxifloxacin and rifampicin respectively as has been demonstrated earlier for all antitubercular drugs.

The efficacy of three drug combination (econazole, moxifloxacin and rifampicin) in free or in encapsulated form against murine tuberculosis is apparent.

TABLE II

Chemotherapeutic efficacy of oral econazole and moxifloxacin-loaded PLG nanoparticles against murine tuberculosis

| Groups | $Log_{10}$ cfu Lung | $Log_{10}$ cfu Spleen |
|---|---|---|
| Untreated controls | 6.88 ± 0.035 | 6.90 ± 0.025 |
| Free econazole twice daily (112 doses) | 4.87 ± 0.040 | 4.89 ± 0.020 |
| Free moxifloxacin once daily (56 doses) | 4.96 ± 0.013 | 4.96 ± 0.013 |
| Free econazole + moxifloxacin (112 doses + 56 doses) | 3.03 ± 0.070 | 3.14 ± 0.130 |
| Free econazole + moxifloxacin + RIF (112 doses + 56 doses + 56 doses) | N.D. | N.D. |
| Free - RIF + INH + PZA + EMB (56 doses) | N.D. | N.D. |
| PLG - econazole weekly (8 doses) | 4.85 ± 0.050 | 4.89 ± 0.040 |
| PLG - moxifloxacin once daily (8 doses) | 4.94 ± 0.013 | 4.96 ± 0.030 |
| PLG - econazole + moxifloxacin (8 doses) | 3.04 ± 0.120 | 3.13 ± 0.140 |
| PLG - econazole + moxifloxacin + RIF (8 doses + 6 doses) | N.D. | N.D. |
| PLG - RIF + INH + PZA + EMB (6 doses) | N.D. | N.D. |

Values are mean ± S.D. of 5 animals

We claim

1. An oral drug delivery system for treatment of tuberculosis comprising:
    a) poly DL-lactide-co-glycolide nanoparticles having enconazole encapsulated therein;
    b) poly DL-lactide-co-glycolide nanoparticles having moxifloxacin encapsulated therein; and
    c) poly DL-lactide-co-glycolide nanoparticles having rifampicin encapsulated therein.

2. The oral drug delivery system of claim 1, wherein the poly DL-lactide-co-glycolide nanoparticles have an average size of 217 nm to 250 nm.

3. The oral drug delivery system of claim 1, wherein poly DL-lactide-co-glycolide nanoparticles have a polydispersity index of 0.38 to 0.4.

* * * * *

UNITED STATES PATENT AND TRADEMARK OFFICE
CERTIFICATE OF CORRECTION

PATENT NO. : 8,409,619 B2  
APPLICATION NO. : 12/682698  
DATED : April 2, 2013  
INVENTOR(S) : Gopal Krishan Khuller et al.

It is certified that error appears in the above-identified patent and that said Letters Patent is hereby corrected as shown below:

On the Title page, item [56]; Column 2, OTHER PUBLICATIONS, Line 3, Delete "Ctir" and insert -- Crit --

In the Claims:

Column 6, Line 28, Claim 1, delete "enconazole" and insert -- econazole --

Signed and Sealed this  
Second Day of July, 2013

Teresa Stanek Rea  
*Acting Director of the United States Patent and Trademark Office*